United States Patent [19]

Copp et al.

[11] Patent Number: 4,465,685
[45] Date of Patent: Aug. 14, 1984

[54] ANTIINFLAMMATORY PYRAZOLE THIOUREAS

[75] Inventors: Frederick C. Copp, Beckenham; Albert G. Caldwell, West Wickham; David Collard, Beckenham, all of England

[73] Assignee: Burroughs Wellcome Co., Research Triangle Park, N.C.

[21] Appl. No.: 331,011

[22] Filed: Dec. 15, 1981

[30] Foreign Application Priority Data

Dec. 23, 1980 [GB] United Kingdom ............... 8041151

[51] Int. Cl.³ ................... A61K 31/47; C07D 401/04
[52] U.S. Cl. .................................. 424/258; 424/263; 424/266; 424/273 P; 546/153; 546/159; 546/162; 546/163; 546/256; 546/279; 548/362
[58] Field of Search .............. 548/362; 546/153, 159, 546/163, 256, 279, 162; 424/258, 263, 266, 273 P

[56] References Cited

U.S. PATENT DOCUMENTS 3,646,059 2/1972 Brantley ............................. 548/362

OTHER PUBLICATIONS

Duffin et al., J. Chem. Soc., 1954, pp. 408-415.

Primary Examiner—Richard A. Schwartz
Attorney, Agent, or Firm—Donald Brown

[57] ABSTRACT

Compounds of formula (I)

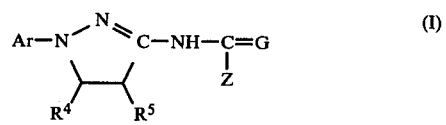

inhibit both the cyclo-oxygenase and lipoxygenase pathways of arachidonic acid oxygenation and are useful in medicine as, e.g., anti-inflammatory and anti-asthmatic agents.

The compounds may be administered as the raw chemical or in association with a carrier as a pharmaceutical formulation.

The compounds may be prepared by methods analogous to those known in the art, e.g. by the method of Duffin and Kendall in J. Chem. Soc. (1954), 408-415, or by other methods.

21 Claims, No Drawings

ANTIINFLAMMATORY PYRAZOLE THIOUREAS

This invention relates to formulations comprising heterocylic compounds and their preparation, to their use in medicine in a mammal, including man, e.g. as anti-inflammatory or anti-allergic agents or as agents in the prevention of tissue rejection, and to certain novel heterocylic compounds and their preparation.

In their studies on the reaction of diazonium salts with 1-aryl-2-pyrazolines Duffin and Kendall (J. Chem. Soc., (1954), 408–415) produced 3-($N^2$-phenylthioureido)-1-phenyl-2-pyrazoline (page 409 and 413) in tests on the product of an earlier reaction. It has now been found that compounds in which the phenyl ring is substituted and other compounds of formula (I) inhibit both the lipoxygenase and cyclo-oxygenase pathways of arachidonic acid metabolism in vitro and are useful as anti-inflammatroy or anti-allergic agents, or as agents in the prevention of tissue rejection and other medical conditions which may be alleviated by the inhibition of these pathways.

Accordingly, the present invention relates to heterocylic compounds of formula (I) and salts thereof:

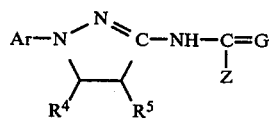

(I)

wherein,

Ar is a monocylic or bicyclic aromatic radical having from 5 to 10 ring atoms selected from carbon and nitrogen optionally substituted in any position of the ring by one or more substituent(s) provided that Ar is other than unsubstituted phenyl;

either G is X and Z is $NRR^1$ or G is NR and Z is $XR^1$ wherein X is O or S; and R, $R^1$, $R^4$ and $R^5$ are each the same or different and are each selected from hydrogen, alkyl, unsubstituted phenyl and Ar as defined above, and R and R' may also be allyl.

Examples of aromatic radicals include substituted-phenyl, naphthyl, quinolyl, benzyl, and pyridyl. Particulary preferred aromatic radicals are phenyl and pyridyl, especially wherein 'pyridyl' is selected from 2-pyridyl and 4-pyridyl.

When in the 1-position of the pyrazoline ring, the aromatic ring is preferably substituted and examples of suitable substituents are halo, alkyl (which may itself be optionally substituted by halo), carboxy, alkoxy, nitro, amino (which may itself be optionally substituted by 1 or 2 alkyl groups), hydroxy and alkylsulphonyl of which the alkyl moiety may itself be optionally substituted by halo. Examples of especially suitable Ar substituents are halo (that is: fluoro, chloro, bromo and iodo) and trifluoromethyl. When Ar is substituted-phenyl, the preferred positions of the ring for any substituent are those selected from the 2-, 3-, 4-, 3,4- and 2,6-positions. For example, Ar may be selected from 3-trifluoromethylphenyl, 4-trifluoromethylphenyl, 4-fluorophenyl, 4-chlorophenyl, 4-bromophenyl, 3-trifluoromethyl-4-fluorophenyl, 3-trifluoromethyl-4-chlorophenyl and 3-trifluoromethyl-4-bromophenyl. When Ar is pyridyl, the preferred position of the ring for any substituent is the 5-position. For example, Ar may be selected from 5-chloro-2-pyridyl, 5-bromo-2-pyridyl and 5-iodo-2-pyridyl.

Preferably, both R and R' are other than allyl.

When any of R, $R^1$, $R^4$ and $R^5$ are Ar or phenyl the aromatic ring is preferably unsubstituted. For example, they may be selected from phenyl, 2-pyridyl and 4-pyridyl. $R^4$ and $R^5$ are preferably selected from hydrogen and alkyl. When Z is $NRR^1$, R and $R^1$ are preferably selected from hydrogen, alkyl, phenyl, 2-pyridyl and 4-pyridyl; and when G is NR and Z is $XR^1$, R and $R^1$ are preferably selected from hydrogen and alkyl. Compounds of formula (I) wherein G is X and Z is $NRR^1$ such as those wherein R is H and $R^1$ is phenyl or alkyl such as methyl are especally preferred.

Examples of compounds of formula (I) are:

3-($N^2$-phenylureido)-1-(3-trifluoromethylphenyl)-2-pyrazoline;

3-($N^2$-3-pyridylureido)-1-(3-trifluoromethylphenyl)-2-pyrazoline;

3-($N^2$-methylureido)-1-(3-trifluoromethylphenyl)-2-pyrazoline;

3-($N^2$-methylthioureido)-1-(3-trifluoromethylphenyl)-2-pyrazoline;

3-($N^2$,S-dimethylisothioureido)-1-(3-trifluoromethylphenyl)-2-pyrazoline;

3-($N^2$,O-dimethylisoureido)-1-(3-trifluoromethylphenyl)-2-pyrazoline;

3-(N-methylthioureido)-1-(5-bromo-6-methyl-2-pyridyl)-2-pyrazoline;

3-(3-butylthioureido)-1-(3-trifluoromethylphenyl)-2-pyrazoline;

N,S-dimethyl-$N^2$-[1-(4-chlorophenyl)-2-pyrazolin-3-yl]isothiourea;

3-(3-methylthioureido)-1-(2-naphthyl)-2-pyrazoline;

3-(3-phenylureido)-1-(3-carboxyphenyl)-2-pyrazoline;

3-(3-methylthioureido)-1-(2-pyridyl)-2-pyrazoline;

3-(3-methylthioureido)-1-(3-quinolyl)-2-pyrazoline;

3-(3-methylthioureido)-1-(2-chlorophenyl)-2-pyrazoline;

3-(3-methylthioureido)-1-(3-t-butylphenyl)-2-pyrazoline;

3-($N^2$,S-dimethylisothioureido)-1-(2-chlorophenyl)-2-pyrazoline;

$N^1$,S-dimethyl-$N^2$-[1-(2-naphthyl)-2-pyrazolin-3-yl]isothiourea;

3-(3-isobutylthioureido)-1-(3-trifluoromethylphenyl)-2-pyrazoline;

3-(3-benzylthioureido)-1-(3-trifluoromethylphenyl)-2-pyrazoline; and 3-(3-allylthioureido)-1-(3-trifluoromethylphenyl)-2-pyrazoline The compounds of formula (I) may be prepared by any method analogous to those known in the art for the preparation of compounds of analogous structure.

(1) A method for the preparation of compounds of formula (I) wherein G is X and Z is $NHR^1$ comprises the reaction of an amine of formula (II) with a compound of formula (III)

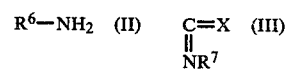

wherein one and only one of $R^6$ and $R^7$ is

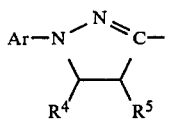

and the other is $R^1$; and Ar, $R^4$, $R^5$, X and $R^1$ are defined as in formula (I). The reaction may be effected in an inert solvent such as chloroform, preferably with heating.

The compound of formula (II) wherein $R^6$ is $R^1$ and the compound of formula (III) wherein $R^7$ is

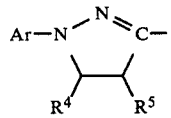

may be prepared by reaction of the compound of formula (II) wherein $R^6$ is

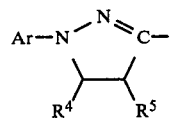

with a compound of formula (IV): $CXR^8R^9$ (IV) wherein X is as defined in formula (III) and $R^8$ and $R^9$ may be the same or different and are each independently selected from halo radicals (e.g. chloro, bromo and iodo).

(2) A method for the preparation of compounds of formula (I) wherein G is NR and Z is $XR^1$ comprises reaction of the corresponding compound of formula (I) wherein G is X and Z is $NHR^1$ with an alkyl halide ($RR^8$ wherein R is as defined in formula (I) and $R^8$ is as defined in formula (IV), supra).

The compounds of formula (I) may be used in the relief of rheumatoid arthritis, rheumatoid spondylitis, osteoarthritis, gouty arthritis and other arthritic conditions, inflamed joints, eczema, other inflammatory skin conditions, inflammatory eye conditions including conjunctivitis, pyresis, pain and other conditions associated with inflammation. Such other conditions associated with inflammation include the reduction of tissue necrosis in chronic inflammation, the suppression of tissue rejection following transplant surgery and ulcerative colitis.

The compounds of formula (I) may also be used in the treatment of prophylaxis of allergic conditions and other airway inflammatory conditions such as asthma and of asthma having a non-allergic origin and bronchitis. The compounds may also be useful as antispasmogenic agents.

The amount required of a compound of formula (I) (hereinafter referred to as the active ingredient) for therapeutic effect will, of course, vary both with the particular compound, the route of administration and the mammal under treatment. A suitable dose of a compound of formula (I) for a mammal suffering from an inflammatory, painful or pyretic condition as defined hereinbefore is 0.5 to 500 mg of base per kilogram bodyweight, the most preferred dosage being 0.5 to 50 mg/kg of mammal bodyweight, for example 5 to 25 mg/kg; administered two or three times daily.

In the case of the treatment of prophylaxis of inflammatory airway conditions, a suitable anti-asthmatic dose of a compound of formula (I) is 1 mg to 10 mg of base per kilogram bodyweight, the most preferred dosage being 10 mg to 5 mg/kg of mammal bodyweight, for example from 1 to 2 mg/kg.

While it is possible for an active ingredient to be administered alone as the raw chemical, it is preferable to present it as a pharmaceutical formulation. Conveniently, the active ingredient comprises from 0.1% to 99.9% by weight of the formulation. Conveniently, unit doses of a formulation contain between 0.1 mg and 1 g of the active ingredient. For topical administration, the active ingredient preferably comprises from 1% to 2% by weight of the formulation but the active ingredient may comprise as much as 10% w/w. Formulations suitable for nasal or buccal administration, (such self-propelling powder-dispensing formulations described hereinafter), may comprise 0.1 to 20% w/w, for example about 2% w/w of active ingredient.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, ophthalmic, rectal, parenteral (including subcutaneous, intramuscular and intravenous), intra-articular, topical, nasal or buccal administration.

The formulations may conveniently be presented in unit dosage form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active or dispersing agent. Moulded tablets may be made by moulding, in a suitable machine, a mixture of the powdered active ingredient and a suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration include liquid or semi-liquid preparations such as liniments, lotions, applications; oil-in-water or water-in-oil emulsions such as creams, ointments or pastes; or solutions or suspensions such as drops. For example, for ophthalmic administration, the active ingredient may be presented in the form of aqueous eye drops as, for example, a 0.1-1.0% solution.

Formulations suitable for administration to the nose or buccal cavity include powder, self-propelling and spray formulations such as aerosols and atomizers. The formulations, when dispersed, preferably have a particle size in the range of 10 to 200u.

Such formulations are most preferably in the form of a finely comminuted powder for pulmonary administration from a powder inhalation device or self-propelling powder-dispensing formulations, where the active ingredient, as a finely comminuted powder, may comprise up to 99.9% w/w of the formulation. In the case of self-propelling solution and spray formulations, the effect may be achieved either by choice of a valve having the desired spray characteristics (i.e. being capable of producing a spray having the desired particle size) or by incorporating the active ingredient as a suspended powder if controlled particle size. Thus the formulation, instead of passing into the lungs, is largely retained in the nasal cavity. These self-propelling formulations may be either powder-dispensing formulations or formulations dispensing the active ingredient as droplets of a solution or suspension.

Self-propelling powder-dispensing formulations preferably comprise dispersed particles of solid active ingredient, and a liquid propellant having a boiling point if below 65° F. (18° C.) at atmospheric pressure. The liquid propellant may be any propellant known to be suitable for medicinal administration and may comprise one or more alkyl hydrocarbons or halogenated lower alkyl hydrocarbons or mixtures thereof; chlorinated and fluorinated lower alkyl hydrocarbons are especially preferred. Generally, the propellant constitutes 50 to 99.9% w/w of the formulation whilst the active ingredient constitutes 0.1 to 20% w/w, for example, about 2% w/w, of the formulation.

The pharmaceutically acceptable carrier in such self-propelling formulations may include other constituents in addition to the propellant, in particular a surfactant or a solid diluent or both. Surfactants are desirable since they prevent agglomeration of the particles of active ingredient and maintain the active ingredient in suspension. Especially valuable are liquid non-ionic surfactants and solid anionic surfactants or mixtures thereof. Suitable liquid non-ionic surfactants are those having a hydrophile-lipophile balance (HLB, see Journal of the Society of Cosmetic Chemists Vol. 1 pp. 311-326 (1949)) of below 10, in particular esters and partial esters of fatty acids with alphatic polyhydric alcohols, for instance, sorbitan monooleate and sorbitan trioleate, known commercially as 'Span 80' (Trade Name) and 'Span 85' (Trade Name), respectively. The liquid non-ionic surfactant may constitute from 0.01 up to 20% w/w of the formulation, though preferably it constitutes below 1% w/w of the formulation. Suitable solid anionic surfactants include alkali metal, ammonium and amine salts of dialkyl sulphosuccinate (where the alkyl groups have 4 to 12 carbon atoms) and alkyl benzene sulphonic acid (where the alkyl group has 8 to 14 carbon atoms). The solid anionic surfactants may constitute from 0.01 up to 20% w/w of the formulation, though preferably below 1% w/w of the composition solid diluents may be advantageously incorporated in such self-propelling formulations where the density of the active ingredient differs substantially from the density of the propellant; also, they help to maintain the active ingredient in suspension. The solid diluent is in the form of a fine powder, preferably having a particle size of the same order as that of the particles of the active ingredient. Suitable solid diluents include sodium chloride, sodium sulphate and sugars.

Formulations of the present invention may also be in the form of a self-propelling formulation wherein the active ingredient is present in solution. Such self-propelling formulations may comprise the active ingredient, propellant and co-solvent, and advantageously an antioxidant stabiliser. The propellant is one or more of these already cited above. Co-solvents are chosen for their solubility in the propellant, their ability to dissolve the active ingredient, and for their having the lowest boiling point consistent with these above-mentioned properties. Suitable co-solvents are lower alkyl alcohols and ethers and mixtures thereof. The co-solvent may constitute 5 to 40% w/w of the formulation, though preferably less than 20% w/w of the formulation. Antioxidant stabilisers may be incorporated in such solution-formulations to inhibit deterioration of the active ingredient and are conveniently alkali metal ascorbates or bisulphites. They are preferably present in an amount of up to 0.25% w/w of the formulation.

Such self-propelling formulations may be prepared by any method known in the art. For example, the active ingredient (either as particles as defined hereinbefore in suspension in a suitable liquid or in up to 20% w/v solution in an acceptable co-solvent, as appropriate) is mixed with any other constituents of a pharamceutically acceptable carrier. The resulting mixture is cooled, introduced into a suitable cooled container and propellant is added thereto in liquid form; and the container is sealed. Alternatively, such self-propelling formulations may be prepared by mixing the active ingredient either in particles as hereinbefore defined or in 2 to 20% w/v alcohol or aqueous solution as appropriate, together with the remaining constituents of the pharmaceutically acceptable carrier other than the propellant; introducing the resulting mixture, optionally with some propellant, into a suitable container; and injecting the propellant, under pressure, into the container at ambient temperature through a valve which comrpises a part of the container and is used to control release of the formualtion from it. Desirably, the container is purged by removing air from it at a convenient stage in the preparation of the self-propelling formulation.

A suitable container for a self-propelling formulation is one provided with a manually-operable valve and constructed of aluminium, stainless steel or reinforced glass. The valve should, of course, be one having the desired spray characteristics of particle size as hereinbefore defined. Advantageously, the valve is of the type which delivers a fixed amount of the formulation on the occasion of each operation of the valve, for example, about 50 to 100 microliters of formulation in each delivery.

Formulations of the present invention may also be in the form of an aqueous or dilute alcoholic solution, optionally a sterile solution, of the active ingredient for use in a nebuliser or atomiser, wherein an accelerated air stream is used to produce a fine mist consisting of small droplets of the solution. Such formulations usually contain a flavouring agent such as saccharin sodium and a volatile oil. A buffering agent such as sodium metabisulphite and a surface active agent may also be included in such a formulation which should also contain a preservative such as methylhydroxybenzoate.

Other formulations suitable for nasal administration include a coarse powder having a particle size of 20 to 500 microns which is administered in the manner if which snuff is taken i.e. by rapid inhalation through the nasal passage from a container of the powder held close up to the nose.

In addition to the aforementioned ingredients, the formulations of this invention may include one or more additional ingredients such as diluents, buffers, flavouring agents, binder, surface active agents, thickeners, lubricants, preservatives eg. methylhydroxybenzoate (including anti-oxidants), emulsifying agents and the like.

Any other therapeutic ingredient may comprise one or more of the following: anti-biotic, anti-fungal and anti-viral agents.

According to the present invention there are therefore provided:

(a) a novel compound of formula (I) or an acid addition salt thereof;

(b) a method for the preparation of the compounds of formula (I);

(c) a pharmaceutical formulation comprising a non-toxic, effective arachidonic acid oxygenation inhibitory amount of a compound of formula (I) or a pharmaceutically acceptable salt thereof a pharmaceutically acceptable carrier therefor;

(d) a method for preparing such formulations;

(e) a method for the prophylaxis or treatment of inflammation in a mammal, including man, comprising the administration to said mammal of a non-toxic, effective anti-inflammatory amount of a compound of formula (I);

(f) a method for the prophylaxis or treatment of pain in a mammal, including man, comprising the administration to said mammal of a non-toxic, effective analgesic amount of a compound of formula (I);

(g) a method for the prophylaxis or treatment of pyresis in a mammal, including man, comprising the administration to said mammal of a non-toxic, effective antipyretic amount of a compound of formula (I);

(h) a method for the prophylaxis or treatment of asthma in a mammal, including man, comprising the administration to said mammal of a non-toxic, effective, antiasthmatic amount of a compound of formula (I);

(i) a method for the inhibition of the lipoxygenase or cyclo-oxygenase pathways of arachidonic acid metabolism comprising the administration of a non-toxic, effective, inhibitory amount of a compound of formula (I) or a pharmaceutically acceptable acid addition salt thereof; and (j) a compound of formula (I) for use in medicine in the inhibition of the lipoxygenase or cyclo-oxygenase pathways of arachidonic acid metabolism The following Examples are provided by way of an illustration of the present invention and should in no way be construed as a limitation thereof. All temperatures indicated are in degrees Celsius.

EXAMPLE 1

Preparation of 3-($N^2$-phenylureido)-1-(3-trifluoromethylphenyl)-2-pyrazoline

A solution of 3-amino-1-(3-trifluoromethylphenyl)-2-pyrazoline (500 mg) and phenylisocyanate (260 mg) in chloroform (10 ml) was heated to reflux for 1 hour. After cooling, the resulting 3-($N^2$-phenylureido)-1-(3-trifluoromethylphenyl)-2-pyrazoline was filtered off and recrystallized from isopropanol, m.p. 230°.

EXAMPLES 2 AND 3

By a method according to that described in Example 1 were prepared the following compounds:

Example 2: 3-($N^2$-methylureido)-1-(3-trifluoromethylphenyl)-2-pyrazoline, m.p. 213°–214°; and Example 3: 3-($N^2$-methylthioureido)-1-(3-trifluoromethylphenyl)-2-pyrazoline, m.p. 241°–242°.

EXAMPLE 4

Preparation of 3-($N^2$-3-pyridylureido)-1-(3-trifluoromethylphenyl)-2-pyrazoline By a method analagous to that described in Example 1, but using n-propanol in place of isopropanol, was prepared 3-($N^2$-3-pyridylureido)-1-(3-trifluoromethylphenyl)-2-pyrazoline which was isolated as a crystalline solid, m.p. 224°.

Analysis: Required: H, 4.04; N, 20.05; C, 55.02. Found: C, 54.90; H, 4.03; N, 19.88.

EXAMPLE 5

Preparation of 3-($N^2$,S-dimethylisothioureido)-1-(3-trifluromethylphenyl)-2-pyrazoline The compound prepared in Example 3 (5 g) and methyliodide (4 ml) in acetone (30 ml) were heated at 65° with stirring. After about 20 minutes all the starting material had dissolved and after a further short time the product started to crystallize out. Heating was continued for 2 hours, then the reaction mixture was cooled in a carbon dioxide bath. The solid product was collected, washed with ethyl acetate and diethyl ether and dried to produce 3-($N^2$,S-dimethylisothioureido)-1-(3-trifluoromethylphenyl)-2-pyrazoline hydriodide monohydrate, m.p. 158°.

Analysis: Required: C, 35.15; H, 3.63; N. 12.61. Found: C, 35.00; H, 3.45; N, 12.64.

EXAMPLE 6

Preparation of 3-(3-methylthioureido)-1-(4-chlorophenyl)-2-pyrazoline

3-Amino-1-(4-chlorophenyl)-2-pyrazoline (1.5 g) (prepared in Reference Example 6 of our European patent specification No. 22-578) and methylisothiocyanate (1.02 g) were heated together at 100° for two hours. The crude product was ground under methanol, collected by filtration, and recrystallised from acetone to yield 3-(3-methylthioureido)-1-(4-chlorophenyl)-2-pyrazoline, m.p. 237°.

EXAMPLE 7

Preparation of 1-(5-bromo-6-methyl-2-pyridyl)-3-(N-methylthioureido)-2-pyrazoline 3-Amino-1-(5-bromo-6-methyl-2-pyridyl)-2-pyrazoline (4.0 g) and methylisothiocyanate (4.7 g) stirred together at about 120°. A clear melt formed which did not solidify very well and which was kept at 120° for 2 hours. The melt was then treated with S.V.M. (15 ml) and stirred whilst cooling. A clear solid resulted which was collected, washed with S.V.M. and dried in vacuo to yield 3.9 g 1-(5-bromo-6-methyl-2-pyridyl)-3-N-methylthioureido-2-pyrazoline, m.p. 229°–230° (decomp).

EXAMPLE 8

Preparation of 3-(3-Butylthioureido)-1-(3-trifluoromethylphenyl)-2-pyrazoline.

Thiophosgene (11.5 g) was added slowly to a solution of 3-amino-1-(3-trifluoromethylphenyl)-2-pyrazoline (23 g) (prepared according to Reference Example 1 of European patent specification No. 22-578) in acetone (250 ml) at 0° in an atmosphere of carbon dioxide. The addition was completed in about 20 minutes and was then allowed to warm to room temperature for 1 hour. The resulting insoluble solid, the hydrochloride of the starting base, was filtered off and washed with fresh acetone. The combined filtrate and washings were evaporated in vacuo to give crude 3-isothiocyanato-1-(3-trifluoromethylphenyl)-2-pyrazoline as a gum (13 g) which subsequently crystallised. This compound was used directly without purification but the presence of the isothiocyanate group was confirmed by infra red spectroscopy which exhibited a broad band in the region of 2005 cm$^{-1}$. This gum (3.8 g) was suspended in toluene (40 ml) and stirred during the addition of butylamine (1.5 g). When the gum changed into a colourless solid. After 2 hours, the mixture was warmed to about 35° for 10 minutes and then cooled back to room temperature. The resulting solid was collected, washed with a little fresh toluene and recrystallised from propanol in long prisms, m.p. 197°–198° of 3-(3-butylthioureido)-1-(3-trifluoromethylphenyl)-2-pyrazoline.

EXAMPLE 9

N,S-Dimethyl-N$^2$/(4-chlorophenyl)-2-pyrazolin-3-yl/isothiourea hydriodide 1-(4-Chlorophenyl)-3-(3-methylthioureido)-2-pyrazoline (436 mg) in acetone (50 ml) was treated with methyliodide (0.2 ml) and heated to reflux for two hours. The reaction mixture was cooled to room temperature and the solid produced collected by filtration.

After recrystallisation from n-propanol the N,S-dimethyl-N$^2$-/1-(4-chlorophenyl)-2-pyrazoline-3-yl/isothiourea hydriodide had m.p. 161°–167°.

EXAMPLE 10

3-(3-Methylthioureido)-1-(2-naphthyl)-2-pyrazoline

3-Amino-1-(2-naphthyl)-2-pyrazoline (1 g) and methylisothiocyanate (1.4 g) were heated at 130° for 7 hours. The cooled reaction mixture was diluted with methanol and the solid product collected by filtration.

After extraction with hot methanol the insoluble 3-(3-methylthioureido)-1-(2-naphthyl)-2-pyrazoline had m.p. 230°–235° decomp.

EXAMPLE 11

1-(3-Carboxyphenyl)-3-(3-phenylureido)-2-pyrazoline

3-Amino-1-(3-carboxyphenyl)-2-pyrazoline (108 mg) and phenylisocyanate (140 mg) in chloroform (10 ml) were heated to reflux overnight. The resultant solid was collected and dried to yield 1-(3-carboxyphenyl)-3-(3-phenylureido)-2-pyrazoline m.p. 255° decomp.

EXAMPLES 12–15

Following the procedure of Example 6, there were prepared:
Example 12: 3-(3-Methylthioureido)-1-(2-pyridyl)-2-pyrazoline, m.p. 224°.
Example 13: 3-(3-Methylthioureido)-1-(3-quinolyl)-2-pyrazoline, m.p. 227°.
Example 14: 1-(2-Chlorophenyl)-3-(3-methylthioureido)-2-pyrazoline, m.p. 204°–205°.
Example 15: 1-(3-t-Butylphenyl)-3-(3-methylthioureido)-2-pyrazoline.

EXAMPLES 16–17

Following the procedure of Example 9, there were prepared:
Example 16: 1-(2-Chlorophenyl)-3-(N$^2$,S-dimethylisothioureido)-2-pyrazoline hydriodide, m.p. 139°–140°.
Example 17: N$^1$,S-Dimethyl-N$^2$-/1-(2-naphthyl)-2-pyrazolin-3-yl/isothiourea hydriodide, m.p. 155°–156°

EXAMPLES 18–20

Following the procedure of Example 8, there were prepared:
Example 18: 3-(3-Isobutylthioureido)-1-(3-trifluoromethylphenyl)-2-pyrazoline, m.p. 215°–216°.
Example 19: 3-(3-Benzylthioureido)-1-(3-trifluoromethylphenyl)-2-pyrazoline, m.p. 209°.
Example 20: 3-(3-Allylthioureido)-1-(3-trifluoromethylphenyl)-2-pyrazoline, m.p. 223°.

EXAMPLE A: TABLET

|  | In one tablet |
| --- | --- |
| Active Ingredient | 5.0 mg |
| Lactose | 82.0 mg |
| Starch | 10.0 mg |
| Povidone | 2.0 mg |
| Magnesium Stearate | 1.0 mg |

Mix together the active ingredient, lactose and starch. Granulate the powders using a solution of Povidone in purified water. Dry the granule, add the magnesium stearate and compress to produce tablets, 100 mg per tablet.

EXAMPLE B: OINTMENT

| Active Ingredient | 1.0 mg |
| --- | --- |
| White Soft Paraffin | to 100.0 g |

Disperse the active ingredient in a small volume of the vehicle. Gradually incorporate this into the bulk to produce a smooth, homogenous product. Fill into collapsible metal tubes.

EXAMPLE C: CREAM FOR TOPICAL USE

| Active Ingredient | 1.0 g |
|---|---|
| Polawax GP 200 | 20.0 g |
| Lanolin Anhydrous | 2.0 g |
| White Beeswax | 2.5 g |
| Methyl Hydroxybenzoate | 0.1 g |
| Distilled Water | to 100.00 g |

Heat the polawax, beeswax and lanolin together at 60° C. Add a solution of methyl hydroxybenzoate. Homogenise using high speed stirring. Allow the temperature to fall to 50°. Add and disperse the active ingredient. Allow to cool with slow speed stirring.

EXAMPLE D: LOTION FOR TOPICAL USE

| Active Ingredient | 1.0 g |
|---|---|
| Sorbitan Monolaurate | 0.6 g |
| Polysorbate 20 | 0.6 g |
| Cetostearyl Alcohol | 1.2 g |
| Glycerin | 6.0 g |
| Methyl Hydroxybenzoate | 0.2 g |
| Purified Water B.P. | to 100.00 ml |

The methyl hydroxybenzoate and glycerin were dissolved in 70 ml of water at 75° C. The sorbitan monolaurate, Polysorbate 20 and cetostearyl alcohol were melted together at 75° and added to the aqueous solution. The resulting emulsion was homogenised, allowed to cool with continuous stirring and the active ingredient added as a suspension in the remaining water. The whole was stirred until homogenous.

EXAMPLE E: EYE DROPS

| Active Ingredient | 0.5 g |
|---|---|
| Methyl Hydroxybenzoate | 0.01 g |
| Propyl Hydroxybenzoate | 0.04 g |
| Purified Water B.P. | to 100.00 ml |

The methyl and propyl hydroxybenzoates were dissolved in 70 ml purified water at 75° and the resulting solution then allowed to cool. The active ingredient was added next and the solution made up to 100 ml with purified water. The solution was sterilised by filtration through a membrane filter 0.22 um pore size and packed aseptically into suitable sterile containers.

EXAMPLE F: INJECTION SOLUTION

| Active Ingredient | 10.0 mg |
|---|---|
| Water for Injections B.P. | to 1.0 ml |

The active ingredient was dissolved in half of the water for injections and then made up to volume and sterilised by filtration. The resulting solution was distributed into ampoules under aseptic conditions.

EXAMPLE G: INHIBITION OF LIPOXYGENASE AND CYCLO-OXYGENASE

In an enzyme assay according to the method of G. Blackwell and R. J. Flower (Br. J. Pharmac., 63: 36OP (1978)), compounds of the invention were found to have and IC$_{50}$ (uM) for inhibition of each of lipoxygenase and cyclo-oxygenase as indicated in Table I:

TABLE I

| Compound | ED$_{50}$ ($\mu$M) | |
|---|---|---|
|  | Cyclo-oxygenase | Lipoxygenase |
| of Example 1 | 3 | 5–10 |
| of Example 2 | 3 | 3 |
| of Example 3 | 1 | 1 |
| of Example 5 | 1 | 1 |
| of Example 6 | 5 | 3 |
| of Example 8 | 10 | 10 |
| of Example 9 | 10 | 10 |
| of Example 10 | 0.25 | 1 |
| of Example 13 | 10 | 10 |
| of Example 14 | 10 | 10 |
| of Example 17 | 1 | 1 |

What is claimed is:

1. A compound of formula (I) or a pharmaceutically acceptable salt thereof:

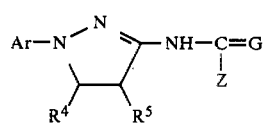

wherein:

Ar is a monocyclic or bicyclic aromatic radical selected from phenyl, naphthyl, quinolyl, benzyl and pyridyl optionally substituted in any position of the ring by one or more substuent(s) selected from fluoro, chloro, bromo, iodo, nitro, carboxy, hydroxy, amino, monoalkyl substituted-amino, dialkyl substituted-amino, trifluoromethyl, monohalo substituted-alkyl, dihalo substituted-alkyl, trihalo substituted-alkyl, lower alkyl, lower alkoxy, alkylsulphonyl, monohalo substituted-alkyl sulphonyl, dihalo substituted-alkyl sulphonyl and trihalo substituted-alkyl sulphonyl provided that Ar is other than unsubstituted-phenyl;

G is S and Z is NRR$^1$; and

R, R$^1$, R$^4$ and R$^5$ are each the same or different and are each selected from hydrogen, lower alkyl, and Ar as defined above; and R and R$^1$ may also be lower alkyl.

2. A compound according to claim 1, wherein R and R$^1$ are each the same or different and are each selected from hydrogen, alkyl, unsubstituted-phenyl and Ar as defined in claim 1; and salts thereof.

3. A compound according to claim 2, wherein Ar is selected from substituted-phenyl, naphthyl, quinolyl, benzyl and pyridyl.

4. A compound according to claim 3 wherein: R$^4$ and R$^5$ are each the same or different and are each selected from hydrogen and lower alkyl.

5. A compound according to claim 4 wherein: R and R$^1$ are each the same or different and are each selected from hydrogen, lower alkyl, phenyl, 2-pyridyl and 4-pyridyl.

6. A compound selected from the group consisting of:
3-(N$^2$-methylthioureido)-1-(3-trifluoromethylphenyl)-2-pyrazoline;
3-(N-methylthioureido)-1-(5-bromo-6-methyl-2-pyridyl)-2-pyrazoline;
3-(3-butylthioureido)-1-(3-trifluoromethylphenyl)-2-pyrazoline;
3-(3-methylthioureido)-1-(2-naphthyl)-2-pyrazoline;

3-(3-methylthioureido)-1-(2-pyridyl)-2-pyrazoline;

3-(3-methylthioureido)-1-(3-quinolyl)2-pyrazoline;

3-(3-methylthioureido)-1-(2-chlorophenyl)-2-pyrazoline;

3-(3-methylthioureido)-1-(3-t-butylphenyl)-2-pyrazoline;

3-(3-isobutylthioureido)-1-(3-trifluoromethylphenyl)-2-pyrazoline;

3-(3-benzylthioureido)-1-(3-trifluoromethylphenyl)-2-pyrazoline; and 3-(3-allylthioureido)-1-(3-trifluoromethylphenyl)-2-pyrazoline.

7. A pharmaceutical formulation, useful in treating inflammation in mammals, comprising an effective amount of a compound or salt of formula (I), as defined in any of claims 1 to 6, in association with a pharmaceutically acceptable carrier therefor.

8. A formulation according to claim 7 in unit dosage form.

9. A formulation according to claim 7 in the form of capsules, tablets, suppositories, liniments, lotions, creams, ointments, drops or aerosols.

10. A formulation according to claim 7 in a form suitable for ophthalmic administration.

11. A formulation according to claim 10 in the form of aqueous eye drops.

12. A formulation according to claim 7, wherein the compound or salt of formula (I) is further in association with another therapeutic ingredient selected from antibiotic, anti-fungal and anti-viral agents.

13. A method for the prophylaxis or treatment of inflammation in a mammal, including man, comprising the administration to said mammal of a non-toxic, effective anti-inflammatory amount of a compound of formula (I), as defined in any of claims 1 to 6.

14. A method according to claim 13, wherein the amount of the compound of formula (I) is from 0.5 to 50 mg per kilogram of mammal bodyweight.

15. A method for the prophylaxis or treatment of pain in a mammal, including man, comprising the administration to said mammal of a non-toxic, effective analgesic amount of a compound of formula (I), as defined in any of claims 1 to 6.

16. A method according to claim 15, wherein the amount of the compound of formula (I) is from 0.5 to 50 mg per kilogram of mammal bodyweight.

17. A method for the prophylaxis or treatment of pyresis in a mammal, including man, comprising the administration to said mammal of a non-toxic, effective anti-pyretic amount of a compound of formula (I), as defined in any of claims 1 to 6.

18. A method according to claim 17, wherein the amount of the compound of formula (I) is from 0.5 to 50 mg per kilogram of mammal bodyweight.

19. A method for the inhibition of the lipoxygenase or cyclo-oxygenase pathways of arachidonic acid metabolism in a mammal, including man, comprising the administration of an effective inhibitory amount of a compound of formula (I), as defined in any of claims 1 to 6.

20. A method according to claim 19, wherein the amount of the compound of formula (I) is from 0.5 to 50 mg per kilogram of mammal bodyweight.

21. A method of treating the medical symptoms of inflammation in a mammal, which symptoms may be alleviated by the inhibition of arachidonic acid metabolism which comprises administering to said mammal an effective arachidonic acid metabolism inhibiting amount of a compound or salt of claim 1.

* * * * *